United States Patent [19]
Van Noy et al.

[11] Patent Number: 5,217,489
[45] Date of Patent: * Jun. 8, 1993

[54] BIFOCAL INTRAOCULAR LENS

[75] Inventors: Stephen J. Van Noy, Fort Worth; Anilbhai S. Patel, Arlington, both of Tex.; Thomas Carncross, Kirkland, Wash.

[73] Assignee: Alcon Surgical, Inc., Fort Worth, Tex.

[*] Notice: The portion of the term of this patent subsequent to Sep. 15, 2009 has been disclaimed.

[21] Appl. No.: 845,300

[22] Filed: Mar. 3, 1992

Related U.S. Application Data

[63] Continuation-in-part of Ser. No. 681,814, Apr. 5, 1991, Pat. No. 5,147,393.

[51] Int. Cl.⁵ .............................................. A61F 2/16
[52] U.S. Cl. ................................................... 623/6
[58] Field of Search ............................. 623/6; 351/161

[56] References Cited

U.S. PATENT DOCUMENTS

| | | | |
|---|---|---|---|
| 4,636,211 | 1/1987 | Nielsen et al. | 623/6 |
| 4,795,462 | 1/1989 | Grendahl | 623/6 |
| 4,813,955 | 3/1989 | Achatz et al. | 623/6 |
| 4,890,913 | 1/1990 | De Carle | 351/161 |
| 5,089,024 | 2/1992 | Christie et al. | 623/6 |

FOREIGN PATENT DOCUMENTS 8902251  3/1989  World Int. Prop. O. .............. 623/6

Primary Examiner—Randy C. Shay
Attorney, Agent, or Firm—Sally S. Yeager; Jeffrey S. Schira

[57] ABSTRACT

Intraocular lenses with three zones for the provision of bifocal vision are described. Methods for the lenses use are also described.

30 Claims, 1 Drawing Sheet

BIFOCAL INTRAOCULAR LENS

This application is a continuation-in-part of U.S. patent application Ser. No. 07/681,814, filed Apr. 5, 1991, now U.S. Pat. No. 5,147,393.

FIELD OF THE INVENTION

The present invention is directed to artificial intraocular lenses with a bifocal optic.

BACKGROUND OF THE INVENTION

The majority of patients undergoing cataract removal receive an intraocular lens which does not provide for both near and distance vision. These patients then usually require some form of refractive correction, such as spectacles or contact lenses to achieve both near (reading) and distance (driving) vision. There is thus a need for intraocular lenses that will enable cataract surgery patients to perform activities requiring near and distance vision, especially in extreme lighting conditions, without spectacles.

Concentric bifocal intraocular lenses are known. U.S. Pat. No. 4,636,211, issued to Nielsen et al., discloses an intraocular lens with concentrically oriented near vision and far vision zones, with the near vision portion centrally positioned and the far vision portion coaxial with and surrounding the near vision portion. U.S. Pat. No. 4,813,955, issued to Achatz et al., discloses a multifocal intraocular lens whose optic portion is divided into near and far range zones such that the rays received by the pupil of the eye pass through near and far range zones of approximately equal areas.

Although prior, concentric, bifocal lenses have optics with portions which will provide for near and distance vision, there can be problems upon implantation due to, among other things, fluctuations in pupil size and spherical aberration phenomenon resulting in non-coincident images from different zones in a lens intended for the same distance correction.

The intraocular lenses of the present invention overcome the aforementioned problems through the use of a three zoned refractive optic for the provision of near and distance vision over the entire human pupil range, especially in extreme lighting conditions, with the peripheral distance zone corrected for spherical aberration such that rays of light passing through the central and peripheral zones form a coincident image in aqueous.

SUMMARY OF THE INVENTION

The lenses of the present invention have an optic portion with a zone surface and a non-zone surface, the zone surface having three zones. A central zone is for distance vision and is approximately 1.5 to 2.0 millimeters (mm) in diameter. A second annular zone is for near vision, and has an inside diameter of about 1.5 to 2.0 mm and an outside diameter of about 2.8 to 3.5 mm. The second zone also has an increased power over the power for distance vision by 2.0–5.0 diopters in aqueous. A third, or peripheral zone, for distance vision, extends from the outer edge of the second zone to the edge of the optic. Additionally, the radius of curvature of the surface of the peripheral zone has been selected with reference to the central zone to correct for spherical aberration as discussed below.

The lenses of the present invention are used to replace the natural lens of the eye when it is necessary to remove the natural lens, usually due to the development of cataracts.

DETAILED DESCRIPTION OF THE PREFERRED EMBODIMENTS

Figure 1:
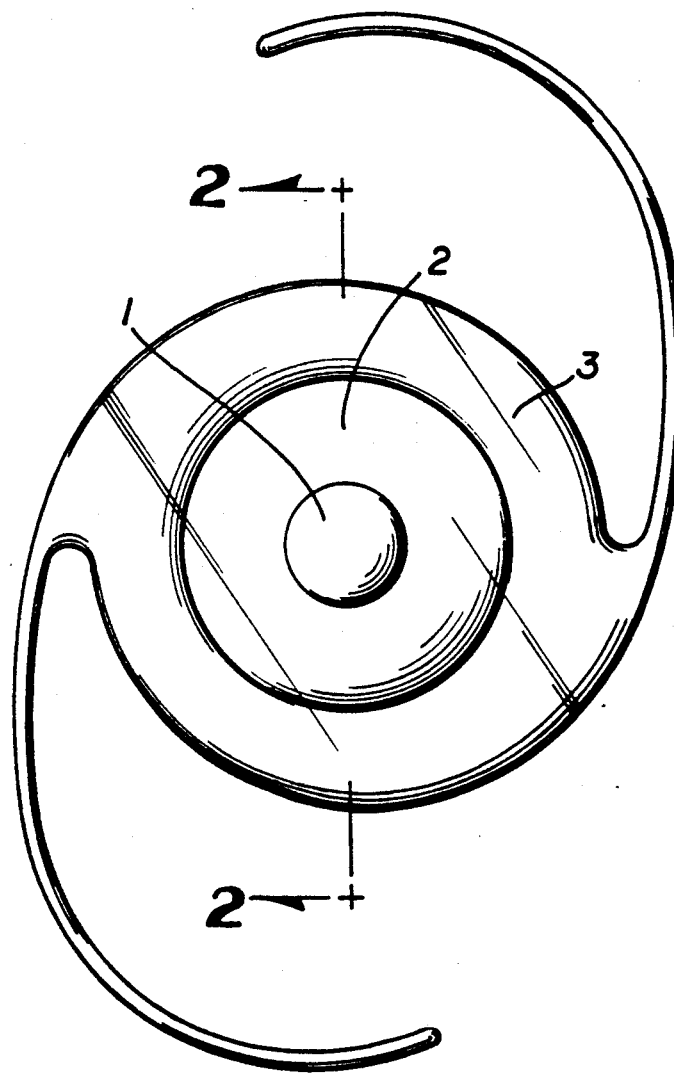
FIG. 1 illustrates the anterior surface of a biconvex, bifocal lens of the present invention.

Intraocular lenses are most frequently implanted in the elderly. Therefore, the lenses of the present invention are designed to best meet the needs of an elderly patient, that is, provide distance vision (greater than 6 meters) throughout the overall pupil range of 1.8–6.5 mm and high resolution near vision (0.35 meters) in a pupil range of 2.5–4.5 mm. To achieve these goals, an intraocular lens with three zones for near and distance vision was created. The intraocular lenses (IOLs) of the present invention can be made of any optically transparent material suitable for an IOL, including, but not limited to, PMMA, soft acrylates (acrylate/methacrylate copolymers), hydrogels, polycarbonates, and silicones. The refractive index of the optical material can range from 1.40 to 1.60. The cross sectional shape of the optic portion of the intraocular lens is not limited, that is, it can be biconvex, plano convex, convex plano, or of a meniscus design. In addition, the optic portion can be of any desired closed shape geometry, including variations of circular geometry, such as oval, such that the lens can be inserted by a surgeon through a relatively small incision in the eye. The dimensions of the optic can be of any size which is suitable for implantation into the eye. The lenses of the present invention can include any suitable shape and number of haptics. Any suitable material for use as haptics can be used. Such materials include, but are not limited to, PMMA, polypropylene, and polyimide. In addition, the lenses can be of a single or multi-piece design. The three zones for near and distance vision are placed on either the anterior or posterior face of the optic, the face containing the three zones will be referred to herein as the "zone surface," the anterior face being that surface of a lens nearest the anterior, or forward, part of the eye and the posterior face, that surface closest to the back or posterior part of the eye. For example, in a biconvex lens, the zones can be placed on either the anterior or posterior surface of the lens. The other surface, not encompassing the zones, referred to herein as the "non-zone surface" can then be manufactured with a single radius of curvature to provide for the additional power so that the total distance and near power of the lens is achieved. The total power of the lens can range from 1 to 35 diopters.

The three zones of the intraocular lenses of the present invention have defined sizes to provide for near and distance vision over the entire pupil range. The size of these zones is not dependent on the cross sectional shape of the optic or the materials used in the lens. The central zone, for distance vision, is approximately 1.5 to 2.0 mm in diameter. The second zone is an annulus surrounding the central zone, and has an inside diameter of about 1.5 to 2.0 mm and an outside diameter of about 2.8 to 3.5 mm. The second zone is for the provision of near vision. The third zone, for the provision of distance vision, surrounds the second zone and extends from the outer diameter of the second zone to the edge of the optic.

All surfaces of the intraocular lens of the present invention are spherical. As previously discussed, the zone surface can be on the anterior or posterior face of the IOL and the non-zone surface will be on the corresponding side. The total power for distance and near vision is determined by these two surfaces of the IOL. Power, in terms of diopters, expresses the ability of the optical lens to bend light rays to a point of focus at a distance from the optic expressed as focal length. Power is inversely proportional to the effective focal length. The distance vision power for the IOL ranges from about 1 to 30 diopters. The central zone radius together with the radius of the non-zone surface determines the power of the distance vision as per the lens maker formula for monofocal IOLs (see American National Standard for Ophthalmics - Intraocular Lenses - Optical and Physical Requirements Z80.7 - 1984). The power for distance vision of the central zone of the three zone surface can be selected from 1 to 30 diopters. The second annular zone radius, together with the radius of the non-zone surface determines the power of the near vision as per the routinely used lens maker formula for monofocal IOLs. The power of the near vision zone provides additional power over the distance power of the central zone. This add power can be in the range of 2 to 5 diopters depending on the patient's eye dimensions and their need. The current state of clinical knowledge indicates that the preferred add power is in the range of 3.5–4.5 diopters. The third zone or peripheral zone radius together with the radius of the non-zone surface determines the focal length for image formation for distance vision from this zone. If the radius of this zone was made identical to that of the central zone for distance vision, then, because of what is referred to in the field of optics as spherical aberration from this peripheral zone, its image would be formed at a shorter focal length and thus, not coincident with the image formed by the central distance zone. If spherical aberration is not corrected, the distance image formed on the retina will be less sharp over a broad range of pupil sizes. In order to correct for this effect and make the two images coincident, it is necessary to increase the radius of the peripheral zone. The determination of the necessary radius of the peripheral zone is done by tracing a ray representing the peripheral zone to form the image on the optical axis at the same location for a ray representing the central zone. The height of the ray used to represent any zone is selected to best approximate the best focus image formed by that zone. The computation of the height of the representative ray is done such that it equally divides the area of the zone. The wave length selected for ray tracing can be in the range of 400–700 nm, but is preferably 550 nm, which represents photopic human vision. Ray tracing can be carried out by various methods known to those skilled in the art of optics, including application of the fundamentals of Snell's law and traditional geometry, or with readily available optical software packages such as GENII®, CODE V™, OSLO®, ACCOS V™, etc.

The radii of curvature of the three zones will vary depending on the type of material used in the optic of the lens. The material used will typically have a refractive index in the range of about 1.4–1.6. For example, when the optic is made of polymethyl methacrylate (PMMA), which has a refractive index of about 1.49, the zones can have radii of curvature as follows. The central zone's radius of curvature can be about 28.5 mm. The second zone's radius of curvature can be between about 14.9–20.9 mm (this provides for about a 2.0–5.0 diopter increase over the distance vision power). The third zone's radius of curvature can be about 30.0 mm. The radius of curvature of the third zone differs from that of the central zone, both of which provide for distance vision, in order to correct for the spherical aberration such that rays passing through the central and third zones form a coincident image in aqueous.

If a soft acrylate copolymer, such as one disclosed in copending U.S. patent application Ser. No. 07/609,863 and the continuation-in-part Application entitled "Polymers and Their Use for Ophthalmic Lenses" filed on Feb. 17, 1992, which comprises 65 wt. % 2-phenylethyl acrylate (PEA), 30 wt. % 2-phenylethyl methacrylate (PEMA), 3.2 wt. % 1,4-butamediol acrylate (BDDA), and 1.8 wt. % 2-(3'methallyl-2'-hydroxy-5'-methyl phenyl)benzotriazole is used to make an IOL of the present invention, then the central zone's radius of curvature can be about 32.0, and the second zone's radius of curvature can be about 24.7 mm–18.4 mm (2.0–5.0 diopter add). The third zone's radius of curvature can be about 33.3, again the radius of curvature of the third zone differs from that of the central zone to correct for spherical aberration.

Figure 2:
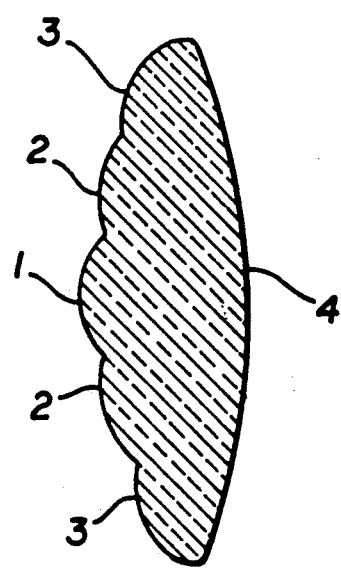
FIG. 2 illustrates a side view of a biconvex, bifocal optic of the present lens invention.

FIGS. 1 and 2 illustrate a preferred embodiment of the present invention. FIG. 1 shows the anterior face of a single piece, PMMA intraocular lens comprising an optic and two haptics. The anterior face of the optic is comprised of three zones to provide for bifocal vision. The first zone (1) is a central zone for the provision of distance vision. It is about 1.8 millimeters in diameter. The second zone (2) is an annulus with an inside diameter of 1.8 mm and an outside diameter of 3.0 mm for the provision of near vision. The third zone (3) surrounds the second zone and extends from the outer diameter of the second zone to the edge of the optic for the provision of distance vision.

FIG. 2 represents a cross sectional view of the optic of FIG. 1 and shows the radii of curvature of the zones. The central zone (1) has a radius of curvature of about 28.5 mm for the provision of distance vision. The second zone has a radius of curvature of 17.4 mm for the provision of near vision (for about a 3.5 diopter increase over the distance vision power). The third zone (3) has a radius of curvature of about 30.0 mm for provision of distance vision. The radius of curvature for the third zone has been adjusted to correct for spherical aberration making light rays passing through the central and third zones form a coincident image in aqueous. The posterior surface of the optic (4) has a radius of curvature to provide for additional power so that the total distance vision power of the lens is from about 1 to about 30 diopters and the total near vision power is 3.0–35.0 diopters. Within these ranges, the near vision power is greater than the distance vision power by 2.0–5.0 diopters.

The lenses of the present invention can be used to replace the natural lens of the eye by a skilled clinician. The natural lens is most usually removed from the elderly upon their development of cataracts.

The present invention, having been fully described, is only limited as set forth in the following claims.

We claim:

1. A bifocal intraocular lens having an optic portion with a zone surface and a non-zone surface, the zone surface comprising a central zone comprising means for the provision of distance vision, having a diameter of about 1.5 to 2.0 mm, a second zone comprising means for the provision of near vision, surrounding the central zone, with an inside diameter of about 1.5 to 2.0 mm and an outside diameter of about 2.8 to 3.5 mm, and a third zone comprising means for the provision of distance vision, which extends from the outer diameter of the second zone to the edge of the optic, the radius of curvature of the third zone differing from that of the central zone to correct for spherical aberration such that images formed by the central and third zones are coincident in aqueous.

2. The lens of claim 1 wherein the central zone has a diameter of 1.8 mm and the second zone has an inside diameter of 1.8 mm and an outside diameter of 3.0 mm.

3. The lens of claim 2 wherein the second zone provides for a 2.0-5.0 diopter power increase over the central and third zones.

4. The lens of claim 2 wherein the optic portion is PMMA and the radius of curvature of the central zone is about 28.5 mm, the radius of curvature of the second zone is about 14.9 mm-20.9 mm, and the radius of curvature of the third zone is about 30.0 mm.

5. The lens of claim 4 wherein the radius of curvature of the second zone is about 17.4 mm.

6. The lens of claim 4 wherein the radius of curvature of the second zone is about 15.7 mm.

7. The lens of claim 1 wherein the second zone provides for a 2.0-5.0 diopter power increase over the central and third zones.

8. The lens of claim 7 wherein the diopter power increase is 3.5-4.5.

9. The lens of claim 1 wherein the optic portion is PMMA and the central zone has a diameter of 1.8 mm and the second zone has an inside diameter of 1.8 mm and an outside diameter of 3.0 mm.

10. The lens of claim 1 wherein the optic is biconvex.

11. The lens of claim 1 wherein the optic is comprised of a material with a refractive index of 1.40 to 1.60.

12. The lens of claim 11 wherein the optic comprises PMMA.

13. The lens of claim 11 herein the optic comprises soft acrylates.

14. A method for providing bifocal vision which comprises, selecting an intraocular lens having an optic portion with a zone surface and a non-zone surface, the zone surface comprising a central zone comprising means for the provision of distance vision, having a diameter of about 1.5 to 2.0 mm, a second zone comprising means for the provision of near vision, surrounding the central zone, with an inside diameter of about 1.5 to 2.0 mm and an outside diameter of about 2.8 to 3.5 mm, and a third zone comprising means for the provision of distance vision, which extends from the outer diameter of the second zone to the edge of the optic, the radius of curvature of the third zone differing from that of the central zone to correct for spherical aberration such that images formed by the central and third zones are coincident in aqueous, and implanting said lens into the eye of a patient.

15. The method of claim 14 wherein said selecting step includes selecting a lens wherein the central zone has a diameter of 1.8 mm, and the second zone has an inside diameter of 1.8 mm and an outside diameter of 3.0 mm.

16. The method of claim 15 wherein said selecting step includes selecting a lens wherein the radius of curvature of the central zone is about 28.5 mm, the radius of curvature of the second zones is about 14.9 mm-20.9 mm, and the radius of curvature of the third zone is about 30.0 mm.

17. The method of claim 16 wherein said selecting step includes selecting a lens wherein the radius of curvature of the second zone is about 17.4 mm.

18. The method of claim 14 wherein said selecting step includes selecting a lens wherein the second zone has a 2.0-5.0 diopter power increase over the central and third zones.

19. The method of claim 18 wherein said selecting step includes selecting a lens wherein the diopter power increase is 3.5-4.5.

20. The method of claim 14 wherein said selecting step includes selecting a lens wherein the optic portion is PMMA and the radius of curvature of the central zone is about 28.5 mm, the radius of curvature of the second zone is about 14.9 mm-20.9 mm, and the radius of curvature of the third zone is about 30.0 mm.

21. The method of claim 20 wherein said selecting step includes selecting a lens wherein the radius of curvature of the second zone is about 17.4 mm.

22. The method of claim 14 wherein said selecting step includes selecting a lens wherein the lens is biconvex.

23. The method of claim 14 wherein said selecting step includes selecting a lens wherein the optic is comprised of a material with a refractive index of 1.40-1.60.

24. The method of claim 14 wherein said selecting step includes selecting a lens wherein the lens is comprised of a soft acrylate.

25. An intraocular lens having an optic portion with a zone surface and a non-zone surface, the zone surface comprising a central zone with a radius of curvature of about 28.5 mm, a second zone having a radius of curvature of about 14.9 mm-20.9 mm, and a third zone having a radius of curvature of about 30.0 mm.

26. The lens of claim 25 having a biconvex optic portion.

27. The lens of claim 25 wherein the optic portion is PMMA.

28. A soft acrylate intraocular lens having an optic portion with a zone surface and a non-zone surface, the zone surface comprising a central zone comprising means for the provision of distance vision, having a diameter of about 1.5 to 2.0 mm, a second zone comprising means for the provision of near vision, surrounding the central zone, with an inside diameter of about 1.5 to 2.0 mm and an outside diameter of about 2.8 to 3.5 mm, and a third zone comprising means for the provision of distance vision, which extends from the outer diameter of the second zone to the edge of the optic, the radius of curvature of the third zone differing from that of the central zone to correct for spherical aberration such that images formed by the central and third zones are coincident in aqueous.

29. The lens of claim 28 wherein the central zone has a diameter of 1.8 mm and the second zone has an inside diameter of 1.8 mm and an outside diameter of 3.0 mm.

30. The bifocal lens of claim 28 wherein the optic portion comprises about 65 wt. % PEA, 30 wt. % PEMA, 3.2 wt. % BDDA, and 1.8 wt. % 2-(3'methallyl-2'hydroxy-5'-methyl phenyl)benzotriazole.

* * * * *